ns Patent [19]

United States Patent [19]

Grosskopf et al.

[11] Patent Number: 4,863,858
[45] Date of Patent: Sep. 5, 1989

[54] RESTRICTION ENDONUCLEAS DRA III

[75] Inventors: Rüdiger Grosskopf, Haar; Christoph Kessler, Munich, both of Fed. Rep. of Germany

[73] Assignee: Boehringer Mannheim GmbH, Mannheim, Fed. Rep. of Germany

[21] Appl. No.: 191,766

[22] Filed: May 3, 1988

Related U.S. Application Data

[63] Continuation of Ser. No. 754,525, Jul. 12, 1985, abandoned.

[30] Foreign Application Priority Data

Jul. 13, 1984 [DE] Fed. Rep. of Germany ....... 3425957

[51] Int. Cl.⁴ .......................... C12P 19/34; C12N 9/22
[52] U.S. Cl. ......................................... 435/91; 435/199
[58] Field of Search ....................... 435/6, 91, 92, 199, 435/253; 536/27

[56] References Cited

PUBLICATIONS deWit, C. M., Dekker, B. M. M., Neele, A. C. and del Vaarb, A. (1985), FEBS Letters, 180(2), 219–223.
Grosskopf, R., Wolf, W. and Kessler, C. (1985), Nucleic Acids Research 13(5), 1517–1528.
Roberts, R. J. (1985), Nucleic Acids Research 13 (suppl), p. 165.

Roberts, R. J. (1984) Nucleic Acids Research 12 (suppl.), p. 167.
Purvis, I. J. and Moseley, B. E. B. (1983) Nucleic Acids Research 11(16), 5467–5474.
Lambda II (Hendrix, R. W., et al., Eds.) (1983), Appendix II, Cold Spring Harbor Laboratory.

Primary Examiner—Thomas G. Wiseman
Assistant Examiner—Charles L. Patterson

[57] ABSTRACT

The present invention teaches a restriction endonuclease which recognizes and cleaves the following palendromic sequence of nucleic acids at that point indicated by the arrows:

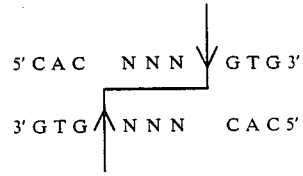

One source of the endonuclease is *Deinococcus radiophilus* (OSM 20551). The endonuclease is useful in analyzing DNA sequences and for preparing DNA fragments for purposes such as making DNA probes.

6 Claims, No Drawings

RESTRICTION ENDONUCLEAS DRA III

This application is a continuation of application Ser. No. 754,525, filed July 12, 1985, now abandoned.

The present invention is concerned with a new Type II restriction endonuclease, Dra III, with a process for obtaining it and with the use thereof.

Type II restriction endonucleases are endodesoxyribonucleases which are able to recognise certain DNA sequences and to cleave them. Phosphodiester bridges are thereby hydrolysed in the target sequence, namely, one in each polynucleotide strand. Therefore, type II restriction endonucleases are valuable for the analysis of DNA molecules.

Admittedly, specific Type II restriction endonucleases are already known for numerous DNA sequences but there is still a need for the provision of further Type II restriction endonucleases which are specific for DNA sequences which have hitherto not been recognised by any of the known restriction endonucleases.

Therefore, it is an object of the present invention to provide a new restriction endonuclease which is able specifically to recognise and to cleave a sequence which has hitherto not been recognised by any such enzyme.

Thus, according to the present invention, there is provided a restriction endonuclease which is characterised by the palindromic recognition sequence:

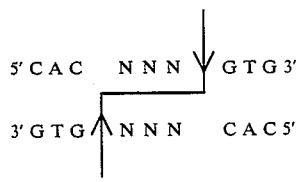

This enzyme preferentially cleaves at the point of cleavage defined by the arrow but other points of cleavage within this sequence are also possible.

The new Type II restriction endonuclease according to the present invention, which in the following is called Dra III, has a temperature optimum at 37° C. and a pH optimum at 8.4. Further optimum reaction parameters are 75 to 150 mM sodium chloride, 8 mM $Mg^{2+}$ and 6 mM β-mercaptoethanol. The presence of $Mg^{2+}$ is necessary for the activity of the enzyme.

An enzyme which is isoschizomeric to Dra III is not known.

As mentioned above, the enzyme acts on palindromic sequences and thus it recognises a self-complementary nucleic acid sequence in which the complementary strand of the double strand has the identical sequence in the opposite-running direction.

The recognition sequence can be confirmed by the complete breakdown of the DNAs of the virus SV40 and of the phages Lambda, fd 109, φX174 and M13mp7 with Dra III.

Dra III cleaves Lambda DNA at the positions 2959, 5618, 6640, 9004, 14482, 30370, 31914, 41484, 47317 and 48439. Fragments thereby result with the length 2959, 2659, 1022, 2364, 5478, 15888, 1544, 9570, 5833, 1122 and 63 base pairs (bp).

Dra III cleaves SV40 DNA at position 2721, fd109RF DNA at position 7598, φX174F DNA at position 5815 and M13mp7 DNA at position 5721.

The fragments specifically obtained by DRA III digestion of the analysed DNAs and clearly demonstrated in agarose and polyacrylamide gels show that Dra III recognised the point of cleavage 5'-CACNNNGTG-3'.

The point of cleavage within the recognition sequence of the enzyme can be ascertained as follows:

The DNA of the modified phage fd109RF is cleaved into two fragments with Bam HI by cleavage in positions 2220 and 7521 (positions referred to the (+) strand). Both strands of the smaller 2983 bp long fragment are terminally marked in two parallel, different reactions. The (+) strand is phosphorylated at the 5' end at position 7522 with gamma ($^{32}P$)ATP and T4 polynucleotide kinase. In the second reaction, the complementary (−) strand is lengthened on the 3' end at position 7526 with alpha($^{32}P$)dGTP and Klenow polymerase by one nucleotide. Thus, the lengthened (−) strand terminates at position 7525. Both differently marked DNAs are subsequently each split with Acc I at position 7968.

From the resulting 5'- and 3'-terminally marked fragments (447(5')/446(3') and 2536(5')/2535(3'); length of the marked individual strands) is isolated the 447(5') and 446(3') fragment, respectively (position 7522 up to and including position 7968(5'), position 7525 up to and including 7970(3'). The 3'-terminally-marked fragment is sequenced. In addition, in each case, an aliquot of the isolated 447(5') and 446(3') fragments, respectively, are split with the enzyme according to the present invention and the length of the 5'- and 3'-marked individual strands, respectively, determined in the sequence gel by comparison with the 3' sequence director. There is thereby given on the 5'-marked strand the cleavage position 7595 and on the 3'-marked strand the cleavage position 7599.

The length determination of the 5'-marked (+) individual strand of the Bam HI-Dra III fragment takes place in the following manner: The (+) individual strand 5'-marked at position 7522 runs identically with the C at position 7602 of the 3' sequence director which corresponds to the first 5'-positioned nucleotide next to the recognition sequence 3'-GTGCATCACC-5'. Therefore, the 5'-marked individual strand terminates with the nucleotide A of the (+) strand at position 7598 (corresponds to the 3' positioned N within the recognition sequence 5'-CACNNNGTG-3'). The point of cleavage of Dra III on the 5'-marked (+) strand is thus between the nucleotides A at position 7598 and G at position 7599.

The length of the complementary 3'-marked (−)-single strand of the Bam HI-Dra III fragment is determined analogously. The (−) single strand 340-marked at position 7525 runs identically with the nucleotide C at position 7596 of the 3' sequence director within the recognition sequence 3'-GTGCATCAC-5' (corresponds to the 3'-positioned N within the recognition sequence 3'-GTGNNNCAC-5'. The 3'-marked single strand ends, therefore, with the nucleotide G of the (−) strand at position 7595 of the recognition sequence. Thus, the point of cleavage of Dra III on the 3'-marked (−) strand is between the nucleotides G at position 7595 and C at position 7596.

According to the present invention, Dra III is obtained by culturing Deinococcus radiophilus DSM 20551 and recovering the enzyme from the cells. For obtaining the enzyme, there can be used the conventional biochemical purification methods, whereby, in the particular fractions obtained, the presence of the enzyme can easily be demonstrated on the basis of the cleavage of its recognition sequence. As substrate, there can be used, for example, lambda DNA. The DNA fragments obtained are separated electrophoretically in agarose gels in the buffer systems conventional for the fragment separation in the presence of ethidium bromide.

The micro-organisms *Deinococcus radiophilus* DSM 20551 used for obtaining the enzyme grows aerobically in TGYM medium ATCC 679. The cells occur individually or in pairs, in non-uniform tetrahedra or cubic bands in more than one plane. The diameter of the cells is 1.0 to 2.5 μm. On agar, pink to red, smooth, slightly convex colonies with uniform edges are formed. The organism is gram-position. The cell walls consist of galactose, glucose, mannose, alanine, glutamic acid, lysine, glucosamine and muramic acid. The main component is a peptidoglycan.

The optimum growth conditions are 10° to 30° C. and pH 7.0, the doubling time being about 2 hours.

In a preferred embodiment of the process according to the present invention, the cells are digested and the extract is centrifuged at 13000 r.p.m. for 45 minutes. For the digestion, there can be used the conventional mechanical methods, for example high pressure dispersion or ultrasonics. High purification of the ammonium sulphate fraction containing the new enzyme can preferably take place by affinity chromatography, chromatography on a molecular sieve and subsequent chromatography over a cation exchanger.

For the affinity chromatography, carrier-fixed heparin, for example heparin-sepharose, has proved to be especially useful.

As molecular sieve material, there has proved useful Ultrogel ACA 54 (LKB), an acrylamide/agarose heteropolymer from 5% acrylamide and 4% agarose. As cation exchanger, there can be used, for example, phosphate, or sulphate group-containing carbohydrates and polystyrenes, for example cellulose phosphate, polystyrene sulphonate and the like.

The following Examples are given for the purpose of illustrating the present invention:

EXAMPLE 1

*Deinococcus radiophilus* DSM 20551 is cultured at 30° C. for 20 hours in TGYM medium (ATCC 679) and harvested in the late log or stationary phase.

TGYM medium has the following composition: 5.0 g. trypton, 1.0 g. glucose, 3.0 yeast extract, 0.5 g. DL-methionine, and 1 liter distilled water.

The yield is about 150 g. of dry mass/100 liters of medium.

50 g. of cell paste are suspended in 100 ml. of digestion buffer (TEMG buffer: 40 mmol/liter tris/HCl (pH 8.0/4° C.); 0.1 mmol/liter EDTA, 7 mmol/liter 2-mercaptoethanol; 10% glycerol). The cells are then digested with ultrasonics (optical density OD$_{578}$ decrease about 40%). Activity about 50,000 U Dra III. The digestion suspension is subsequently centrifuged for 45 minutes at 13000 r.p.m. and at 4° C. The precipitate is discarded, the enzyme being present in the supernatant.

EXAMPLE 2

The supernatant obtained according to Example 1 is chromatographed over a heparin-sepharose column (3×10 cm.). After washing with 5 volumes of TEMG buffer, the enzyme is eluted with a linear gradient with 0 to 1.0 mol/liter sodium chloride. The enzyme appears in the fractions with 0.5 to 0.65 mol/liter sodium chloride. The fractions are combined and precipitated with solid ammonium sulphate (ammonium sulphate end concentration 80% saturation/4° C.).

After precipitating overnight, the ammonium sulphate precipitate is centrifuged off (4° C., 1 hour at 13000 r.p.m.) and taken up in about 5 ml. TEMG buffer+0.5M sodium chloride. Subsequently, it is chromatographed over an Ultrogel ACA 54 column (2×100 cm.) in TEMG+0.5M sodium chloride. The fractions with pure Dra III activity (i.e. in case of incubation for one hour, only the Dra III-specific cleavage pattern occurs on lambda DNA) are combined and dialysed against TEMG buffer. The dialysate is chromatographed over a phosphocellulose column (1×10 cm.).

After washing with 5 volumes of TEMG buffer, it is eluted with a linear gradient with 0 to 0.1 mol/liter sodium chloride. The enzyme appears in the fractions with 0.35 to 0.5 mol/liter sodium chloride. The active fractions are combined and dialysed against 20 mmol/liter tris/HCl buffer (pH 8.0) containing 0.1 mmol/liter EDTA, 10 mmol/liter 2-mercaptoethanol, 100 mmol/liter sodium chloride, 50% glycerol and 0.01% thesit. There are thus obtained about 5000 U Dra III.

ACTIVITY DETERMINATION

Unit Definition

1 U Dra III completely cleaves 1 μg. lambda DNA within 1 hour at 37° C. in 25 μl.

Into a mixture of 13 μl. incubation buffer, containing 0.02 mol/liter tris/HCl, pH 8.4/37° C., 0.02 mol/liter magnesium chloride, 0.2 mol/liter sodium chloride and 0.0212 mol/liter 2-mercaptoethanol are introduced 7 μl. water and 5 μl. lambda DNA (4 OD/ml. extinction (optical density)), as well as 1 μl. Dra III solution (1U/μl.). The solution is maintained at 37° C. for 1 hour, cooled on ice and mixed with 5 μl. of a stop solution containing 7 mol/liter urea, 20% w/v saccharose, 0.06 mol/liter EDTA and 0.01% w/v bromophenol blue. It is then separated electrophoretically on 1% agarose gel for 3 to 4 hours at 100 V. The bands obtained are identified in comparison with DNA length standards.

We claim:

1. A restriction endonuclease which recognizes palindromic sequence

and cleaves said sequence between the third and fourth base from the 3' end.

2. Restriction endonuclease according to claim 1, characterised by a temperature optimum at 37° C. and a pH optimum at 8.4.

3. Method for producing a DNA fragment comprising contacting a sample of DNA with a restriction endonuclease which recognizes palindromic sequence:

and cleaves said sequence at a point between the third and fourth base from the 3' end under conditions favoring action of said endonuclease and obtaining DNA fragments resulting from action of said endonuclease.

4. Method of claim 3 wherein said endonuclease is DRA III.

5. Method of claim 3, wherein said conditions are a temperature of about 37° C. and a pH of about 8.4.

6. Endonuclease of claim 1, wherein said endonuclease is purified from cultured *Deinococcus radiophilus* DSM 20551.

\* \* \* \* \*